United States Patent [19]
Astle

[11] Patent Number: 5,789,251
[45] Date of Patent: Aug. 4, 1998

[54] MULTI-WELL BIOASSAY TRAY WITH EVAPORATION PROTECTION AND METHOD OF USE

[76] Inventor: Thomas W. Astle, 607 Harborview Rd., Orange, Conn. 06477

[21] Appl. No.: 260,719

[22] Filed: Jun. 16, 1994

[51] Int. Cl.$^6$ ............................ G01N 35/02; C12M 1/22
[52] U.S. Cl. .................. 436/48; 436/180; 422/102; 422/104; 435/305.3; 435/305.4
[58] Field of Search ................. 422/99, 102, 104; 436/48, 809, 180; 604/415; 220/229; 435/305.3, 305.4

[56] References Cited

U.S. PATENT DOCUMENTS

| | | | |
|---|---|---|---|
| 3,754,434 | 8/1973 | Guild | 73/863.1 |
| 4,040,234 | 8/1977 | Stockdale et al. | 53/38 |
| 4,719,087 | 1/1988 | Hanaway | 422/102 |
| 4,847,050 | 7/1989 | Jenkins et al. | 422/102 |
| 4,963,493 | 10/1990 | Daftsios | 435/287 |
| 5,112,574 | 5/1992 | Horton | 422/102 |
| 5,133,939 | 7/1992 | Mahe | 422/104 |
| 5,147,065 | 9/1992 | Rush et al. | 220/709 |
| 5,163,583 | 11/1992 | Whitworth | 222/1 |
| 5,290,521 | 3/1994 | DeStefano, Jr. | 422/99 |
| 5,318,753 | 6/1994 | Honda | 422/104 |
| 5,326,534 | 7/1994 | Yamazaki et al. | 422/102 |
| 5,392,914 | 2/1995 | Lemieux et al. | 206/499 |
| 5,397,023 | 3/1995 | Toczek et al. | 220/709 |

Primary Examiner—Nina Bhat
Attorney, Agent, or Firm—John H. Crozier

[57] ABSTRACT

A biopsy apparatus, including: a microplate having defined therein a plurality of vertical wells; and a layer of film disposed over the vertical wells to prevent the evaporation of liquid therefrom, the layer of film being penetrable by a pipette tip to access one of the vertical wells to add liquid to or withdraw liquid from the vertical well, the layer of film being resealable to reseal the area of penetration of the pipette tip when the pipette tip is withdrawn, in order to prevent evaporation of liquid from the vertical well.

13 Claims, 5 Drawing Sheets

MULTI-WELL BIOASSAY TRAY WITH EVAPORATION PROTECTION AND METHOD OF USE

BACKGROUND OF THE INVENTION

1. Field of the Invention

The present invention relates to multi-well bioassay trays generally and, more particularly, but not by way of limitation, to a novel multi-well bioassay tray which has a resealable evaporation protection layer.

2. Background Art

In the field of biotechnology and pharmaceutical research, the de facto standard receptacle for conducting biological assays is a multi-well plate. This is commonly a 96-well plate or subsets of 24 or 48 wells. As the technology has advanced, the volume of reagents required in each well has decreased. Tests that used to consume 1 ml. of reagents decreased the volume to 100 mml. of reagents. Presently, that volume is being decreased to the next order of magnitude, using 1 to 5 mml.

Most of these assays require some period of reaction time for the combined reagents, and this is usually at an elevated temperature, often 37 degrees Centigrade. As the working volume decreases, evaporation becomes an increasing concern and the plates require sealing means to prevent evaporation. Injection molded lids can be used for the plates, but this results in additional cost for the lids. However, with the use of lids and humidity control in the incubator, the evaporation problem is at least controllable.

Another common method of preventing evaporation is to seal the plates with pressure sensitive tape; however, this requires time and labor. Another disadvantage of this method is that the majority of assays require further addition of reagents after periods of incubation. This means removing the sealing tape to permit pipetting additional reagents into the wells. Not only is additional time and labor required, but there is a potential for loss of reagents: as the tape is peeled away, a static electricity charge is created that attracts droplets of reagents from the well. This has an obvious deleterious effect on the assay.

One product which addresses the evaporation problem is an aluminum foil sheet with pressure sensitive adhesive which is placed over the top of the plate. This satisfactorily seals the plate, but a relatively high degree of force is required to puncture the foil with pipette tips to simultaneously access all 96 wells and the foil is not self sealing after being punctured.

Accordingly, it is a principal object of the present invention to provide means and method for sealing multi-well bioassay trays which permit easy access to the contents of the wells.

It is a further object of the invention to provide means and method for sealing multi-well bioassay trays which permit access to he contents of the wells and which automatically reseals the wells after such access.

It is a further object of the invention to provide means and method for sealing multi-well bioassay trays which are economical and easily employed.

Other objects of the present invention, as well as particular features, elements, and advantages thereof, will be elucidated in, or be apparent from, the following description and the accompanying drawing figures.

SUMMARY OF THE INVENTION

The present invention achieves the above objects, among others, by providing, in a preferred embodiment, a bioassay apparatus, comprising: a microplate having defined therein a plurality of vertical wells; and a layer of film disposed over said vertical wells to prevent the evaporation of liquid therefrom, said layer of film being penetrable by at least one pipette tip to access at least one of said vertical wells to add liquid to or withdraw liquid from said at least one of said vertical wells, said layer of film being resealable to reseal the area of penetration of said at least one pipette tip when said at least one pipette tip is withdrawn, in order to prevent evaporation of liquid from said at least one of said vertical wells.

BRIEF DESCRIPTION OF THE DRAWING

Understanding of the present invention and the various aspects thereof will be facilitated by reference to the accompanying drawing figures, submitted for purposes of illustration only and not intended to define the scope of the invention, on which.

DETAILED DESCRIPTION OF THE PREFERRED EMBODIMENTS

Figure 1:
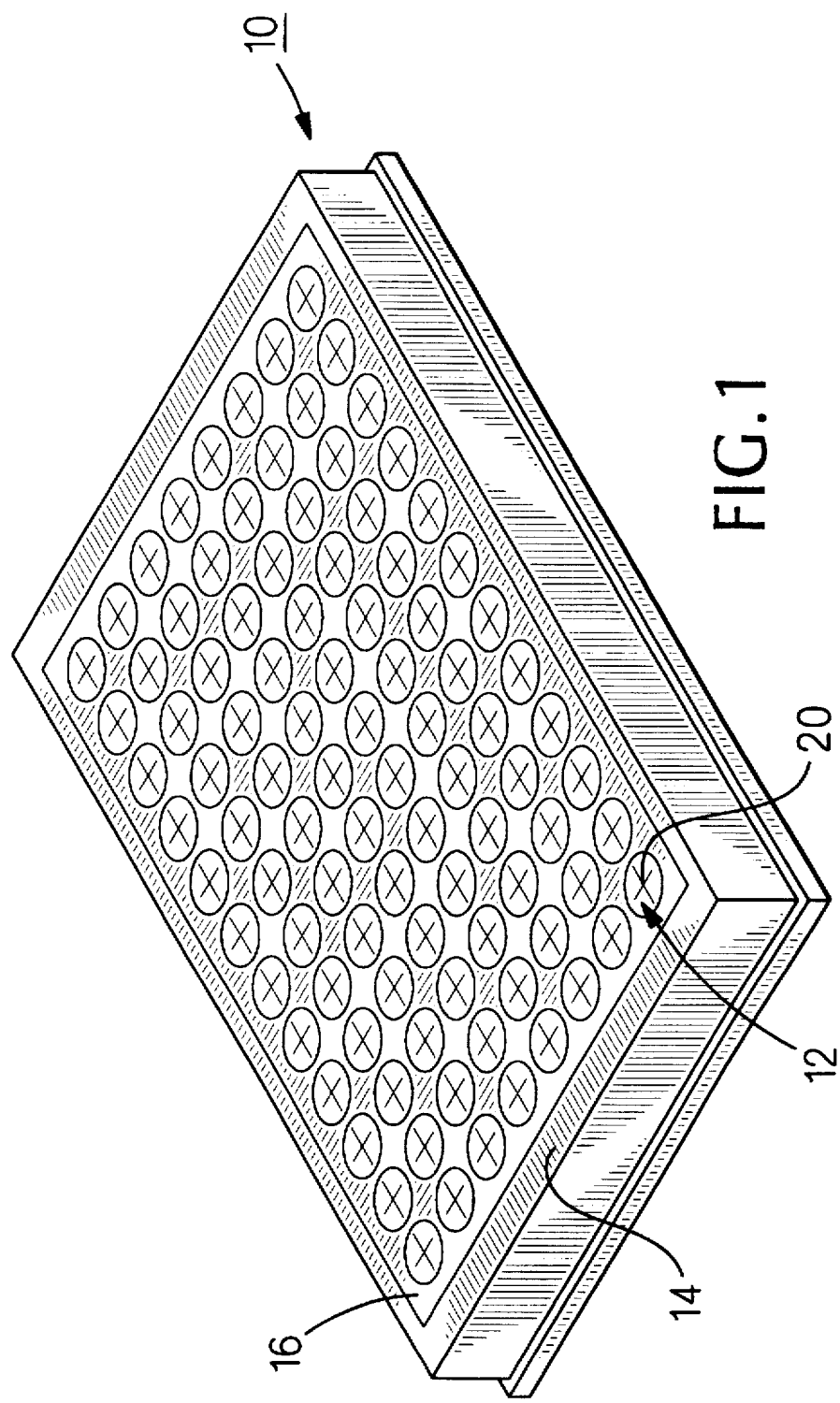
FIG. 1 is an isometric view of a 96-well bioassay microplate with a sealing device of the present invention in place thereon.

Reference should now be made to the drawing figures, on which similar or identical elements are given consistent identifying numerals throughout the various figures thereof, and on which parenthetical references to figure numbers direct the reader to the view(s) on which the element(s) being described is (are) best seen, although the element(s) may be seen also on other views.

Figure 5:
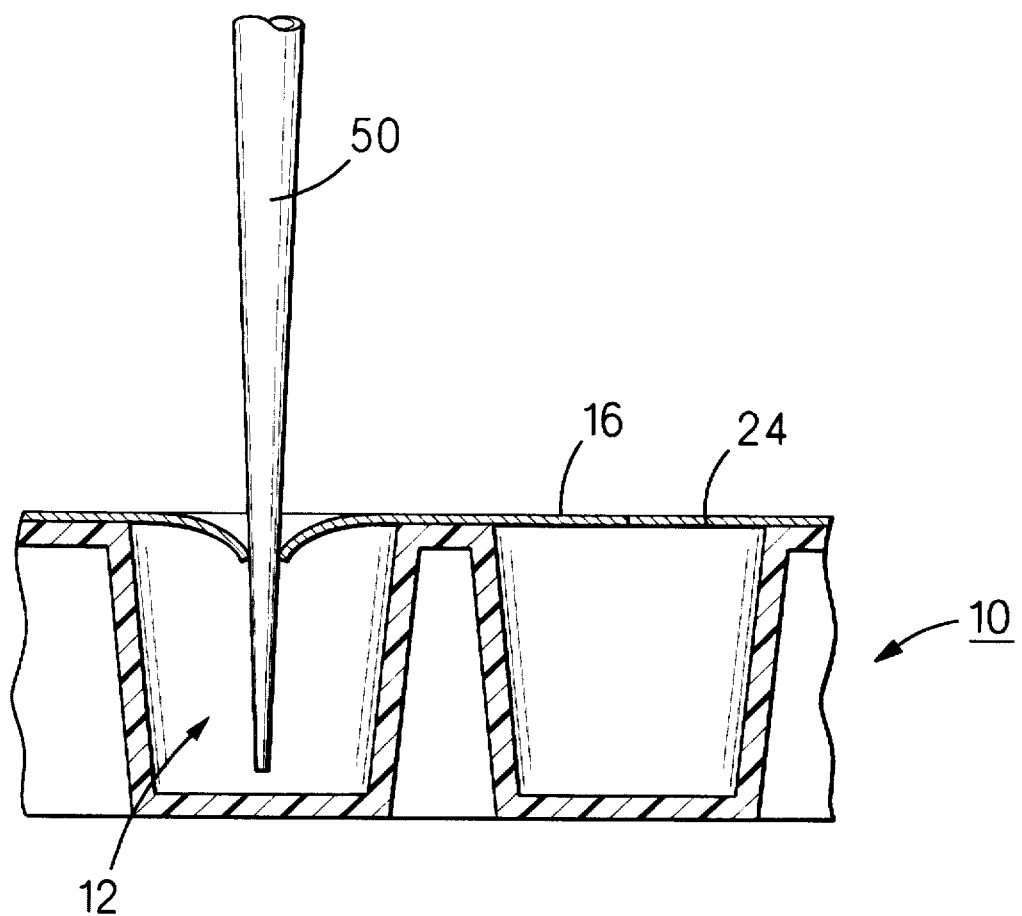
FIG. 5 is an enlarged, side elevational view, partially in cross-section, of the microplate with a pipette tip penetrating the sealing device of the present invention.

FIG. 1 illustrates a conventional 96-well bioassay microplate 10 having defined therein vertical wells, as at 12. It may be assumed that each well 12 is dimensioned to hold therein a working volume of 100 mml. or less of reagents (not shown), although the present invention is applicable to wells of any size. It will be appreciated that, without a suitable covering or sealing means, reagents in wells 12 will tend to evaporate, especially at elevated temperatures, as is described above. The present invention prevents such evaporation by providing over the upper surface 14 of microplate 10 a layer of film 16 attached to the upper surface with a pressure sensitive adhesive 24 (FIG. 5). Film 16 has a plurality of crossed slits, as at 20, defined therein with the film positioned on upper surface 20 such that crossed slits are disposed over each well 12.

Figure 2:
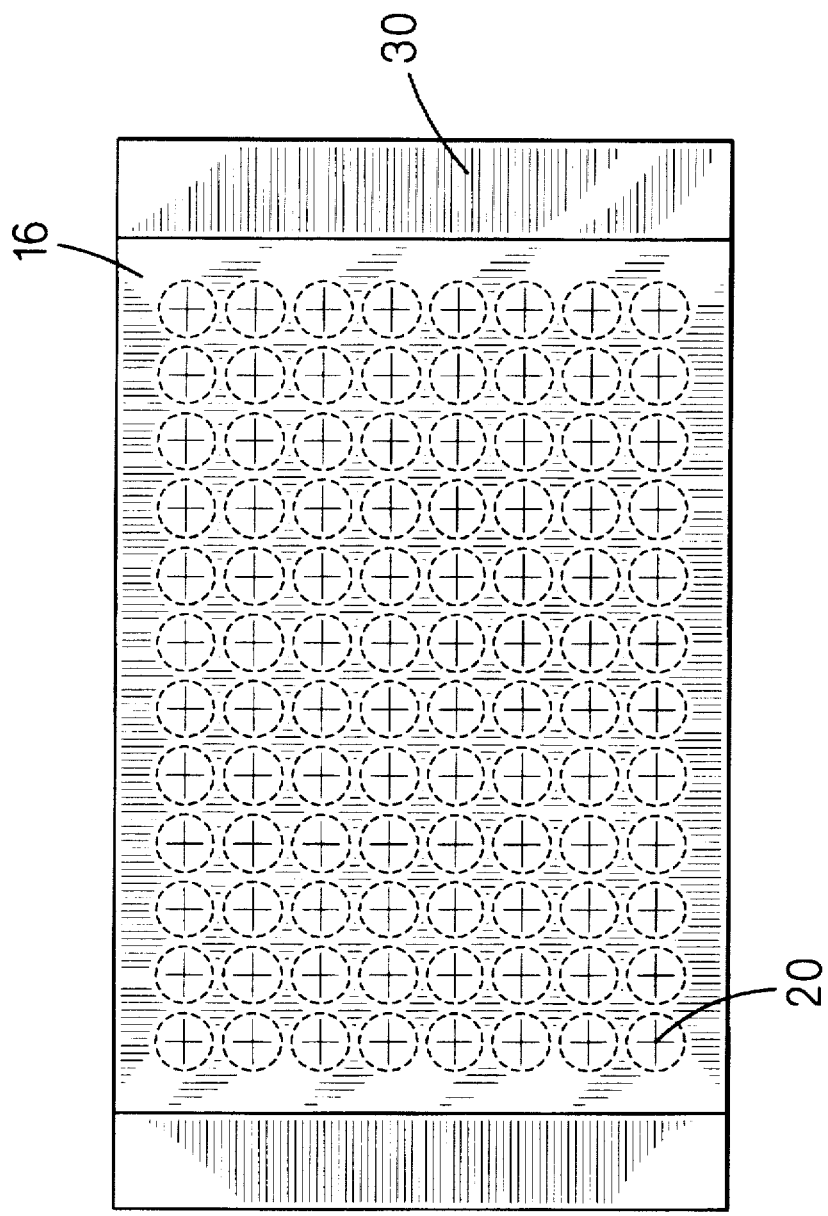
FIG. 2 is a top plan view of the sealing device of the present invention before being placed on the microplate.

FIG. 2 illustrates film 20 as it would be supplied to the user, with the film being disposed on a sheet of release paper 30. In use, film 20 is manually stripped from release paper 30 and is then manually aligned on upper surface 14 (FIG. 1) of microplate 10 and pressed into place, with crossed slits 20 disposed over each well 12, thus sealing the wells against evaporation of any reagents therein.

Figure 3:
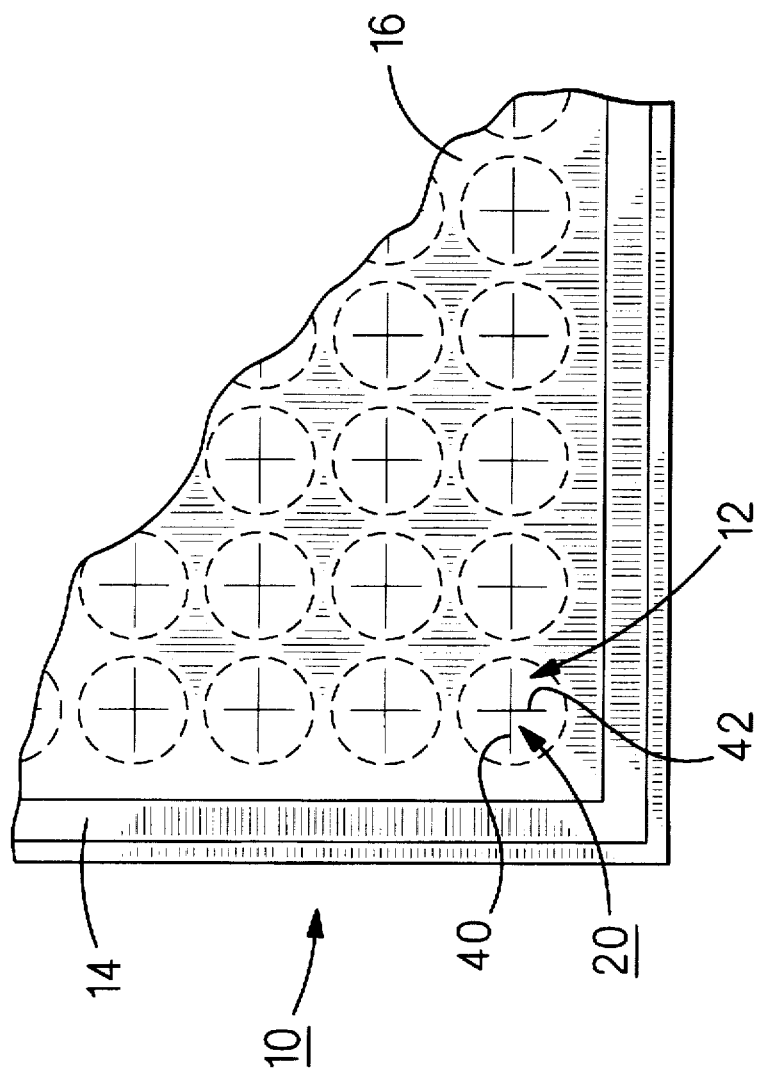
FIG. 3 is an enlarged, fragmentary, top plan view of the microplate of FIG. 1.

Referring to FIG. 3, it can be seen that each set of crossed slits 20 comprises a long slit 40 extending about the length of the inside diameter of a well 12 and parallel to the long axis of microplate 10 (FIG. 1) and a short slit 42 extending about 75% of the inside diameter of the well and parallel to the short axis of the microplate. Long slit 40 permits a pipette tip (not shown) to move sideways within well 12 to "touch off" its orifice on the sidewall of the well, without tearing film 16. By having short slit 42 only about 75% of the diameter of well 12 leaves the remaining about 25% as support for the portion of film 16 spanning the well.

Film 16 is preferably of a material having a high modulus or stiffness, such as clear polyester film in three to four mil thickness. With such a material, crossed slits 20 remain closed by virtue of the support provided by the surrounding area of film 16. Film 16 can be economically die cut to the appropriate size for microplate 10 (FIG. 1). Concurrently with this die cutting procedure, slits 20 are also die cut.

Figure 4:
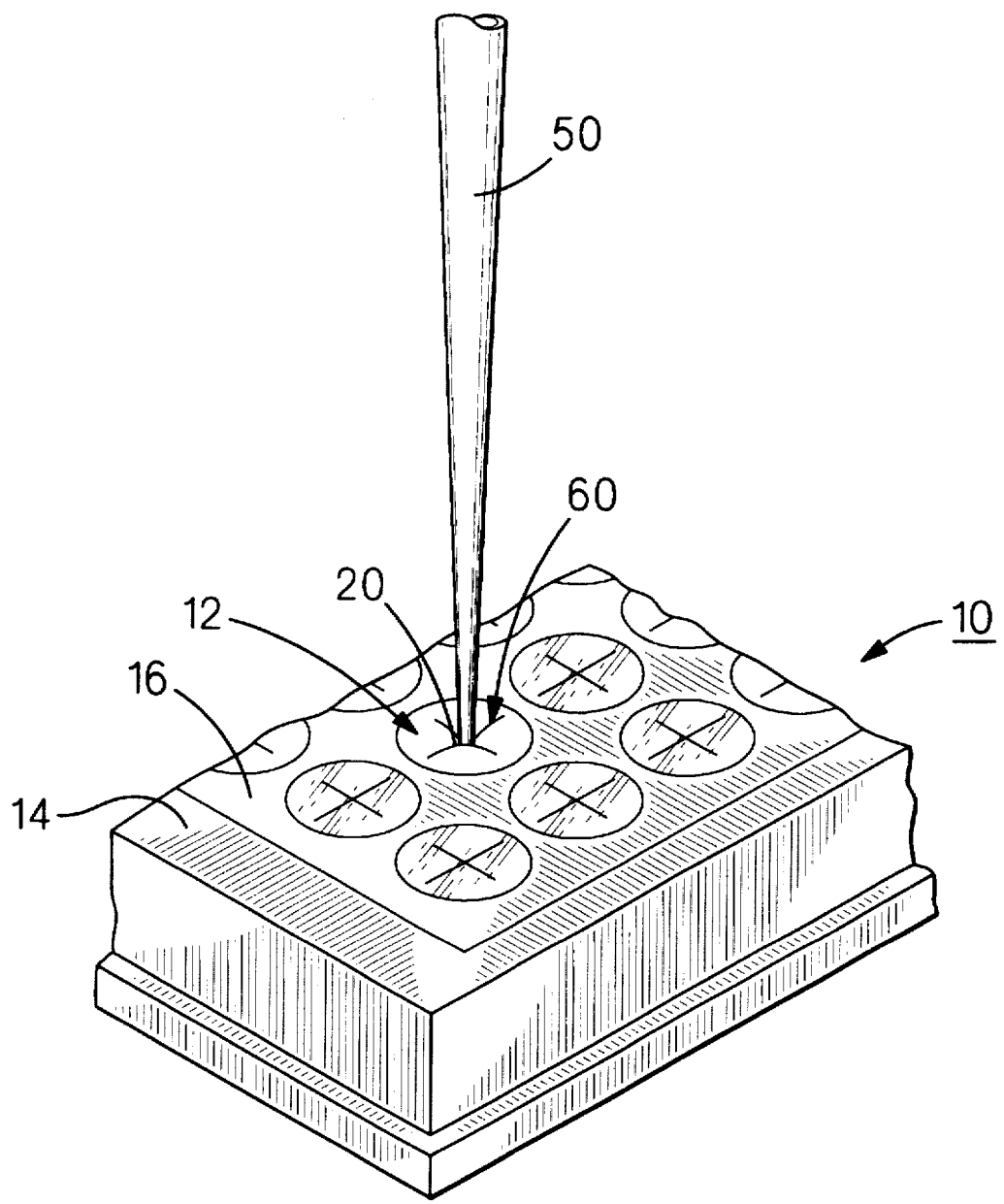
FIG. 4 is an enlarged, fragmentary, isometric view of the microplate with a pipette tip penetrating the sealing device of the present invention.

FIGS. 4 and 5 illustrate film 16 being penetrated through crossed slits 20 over a well 12 by a pipette tip 50 to permit reagents to be added to or withdrawn from the well. All wells 12 in microplate 10 can be so accessed simultaneously with minimal force. This permits all of the presently used pipetting methods, manual or automated, to be employed with the present invention. As pipette tip 50 enters crossed slits 20, it opens them, leaving a small gap 60 (shown enlarged, FIG. 4). Gap 60 allow replacement air to enter or to leave sealed well 12, to compensate for the volume of liquid (not shown) that is being added or withdrawn. As pipette tip 50 is withdrawn, the stiffness of film 16, together with the upward motion of the leaving pipette tip, causes slits 20 to resume the original, or closed, position, essentially resealing well 12.

The sealing device and method of the present invention are economically and easily employed.

It will thus be seen that the objects set forth above, among those elucidated in, or made apparent from, the preceding description, are efficiently attained and, since certain changes may be made in the above construction without departing from the scope of the invention, it is intended that all matter contained in the above description or shown on the accompanying drawing figures shall be interpreted as illustrative only and not in a limiting sense.

It is also to be understood that the following claims are intended to cover all of the generic and specific features of the invention herein described and all statements of the scope of the invention which, as a matter of language, might be said to fall therebetween.

I claim:

1. A bioassay method, comprising:
   (a) providing a microplate having defined therein a plurality of vertical wells;
   (b) providing a layer of film disposed over said vertical wells to prevent the evaporation of liquid therefrom;
   (c) penetrating said layer of film, through slit means defined in said layer of film over at least one of said vertical wells, by at least one pipette tip to access said at least one of said vertical wells to add liquid to or withdraw liquid from at least one of said vertical wells, said slit means defining a plurality of adjacent segments, and said layer of film being penetrated by said at least one pipette tip engaging edges of said segments and bending said edges downwardly toward said at least one of said vertical wells, thus forming an opening in said layer of film so that said at least one pipette tip accesses said at least one of said vertical wells; and
   (d) withdrawing said at least one pipette tip from said layer of film, with said layer of film resealing the area of penetration of said at least one pipette tip when said at least one pipette tip is withdrawn, by said edges returning to their original positions, in order to prevent evaporation of liquid from said at least one of said vertical wells.

2. A bioassay method, as defined in claim 1, further comprising: penetrating said layer of film simultaneously with a plurality of pipette tips to access any selected number of said vertical wells.

3. A bioassay method, as defined in claim 1, further comprising: attaching said layer of film to the upper surface of said microplate over said vertical wells with a pressure sensitive adhesive.

4. A bioassay method, as defined in claim 1, further comprising: penetrating said layer of film through slit means including a long slit defined through said film and extending about the length of the inside diameter of said at least one vertical well and a short slit defined through said film and extending about 75% of the inside diameter of said at least one vertical well, said long and said short slits being orthogonal to one another.

5. A bioassay method, as defined in claim 1, further comprising: providing said layer of film as clear polyester film in three to four mil thickness.

6. A bioassay method, as defined in claim 1, further comprising the step of moving said at least one pipette tip sideways along said slit means and within said at least one of said vertical wells to "touch off" the orifice of said at least one pipette tip on the sidewall of said at least one of said vertical walls.

7. A bioassay method, as defined in claim 1, further comprising:
   (a) providing said slit means defining a plurality of adjacent segments having apexes joined at a common point;
   (b) said layer of film is penetrated by said at least one pipette tip engaging said apexes and bending said apexes downwardly toward said at least one of said vertical wells, thus forming an opening in said layer of film; and
   (c) said layer of film is resealed to reseal the area of penetration of said at least one pipette tip when said at least one pipette tip is withdrawn, by said apexes of said segments returning to their original position.

8. A bioassay apparatus, comprising:
   (a) a microplate having defined therein a plurality of vertical wells;
   (b) a layer of film disposed over said vertical wells to prevent the evaporation of liquid therefrom, said layer of film being penetrable, through slit means defined in said layer of film over at least one of said vertical wells, by at least one pipette tip to access said at least one of said vertical wells to add liquid to or withdraw liquid from said at least one of said vertical wells;
   (c) said slit means defining a plurality of adjacent segments;
   (d) said layer of film being penetrable by said at least one pipette tip engaging edges of said segments and bending said edges downwardly toward said at least one of said vertical wells, thus forming an opening in said layer of film so that said at least one pipette tip can access said at least one of said vertical wells; and
   (e) said layer of film being resealable to reseal the area of penetration of said at least one pipette tip when said at least one pipette tip is withdrawn, by said edges of said segments returning to their original positions, in order to prevent evaporation of liquid from said at least one of said vertical wells.

9. A bioassay apparatus, as defined in claim 8, wherein: said layer of film is penetrable simultaneously by a plurality of pipette tips to access any selected number of said vertical wells.

10. A bioassay apparatus, as defined in claim 8, wherein: said layer of film is attached to the upper surface of said microplate over said vertical wells with a pressure sensitive adhesive.

11. A bioassay apparatus, as defined in claim 8, wherein: said slit means includes a long slit defined through said film and extending about the length of the inside diameter of said at least one vertical well and a short slit defined through said film and extending about 75% of the inside diameter of said at least one vertical well, said long and said short slits being orthogonal to one another.

12. A bioassay apparatus, as defined in claim 8, wherein: said layer of film is clear polyester film in three to four mil thickness.

13. A bioassay apparatus, as defined in claim 8, wherein:
(a) said slit means defines a plurality of adjacent segments having apexes joined at a common point;
(b) said layer of film is penetrable by said at least one pipette tip engaging said apexes and bending said apexes downwardly toward said at least one of said vertical wells, thus forming an opening in said layer of film; and
(c) said layer of film is resealable to reseal the area of penetration of said at least one pipette tip when said at least one pipette tip is withdrawn, by said apexes of said segments returning to their original position.

* * * * *